United States Patent [19]

Nicholas

[11] Patent Number: 5,159,113
[45] Date of Patent: Oct. 27, 1992

[54] PROCESS FOR THE PALLADIUM-CATALYZED AMIDATION OF VINYL CHLORIDE

[75] Inventor: Peter P. Nicholas, Broadview Heights, Ohio

[73] Assignee: The B. F. Goodrich Company, Brecksville, Ohio

[21] Appl. No.: 161,710

[22] Filed: Feb. 29, 1988

Related U.S. Application Data

[63] Continuation-in-part of Ser. No. 683,840, Dec. 19, 1984, abandoned.

[51] Int. Cl.$^5$ .......................................... C07C 231/10
[52] U.S. Cl. ................................... 564/132; 564/205
[58] Field of Search ............................ 564/132, 205

[56] References Cited

U.S. PATENT DOCUMENTS

| | | | |
|---|---|---|---|
| 3,988,358 | 10/1976 | Heck | 260/465 |
| 3,991,101 | 11/1976 | Knifton | 260/486 |
| 4,128,554 | 12/1978 | Heck | 546/317 |

FOREIGN PATENT DOCUMENTS

| | | | |
|---|---|---|---|
| 0498757 | 12/1953 | Canada | 564/205 |
| 723006 | 2/1955 | United Kingdom | 564/205 |

OTHER PUBLICATIONS

Mori et al., *J. Org. Chem.*, 1983, 48, 4058-67.
Breinet et al., *J. Org. Chem:*, 1983, 48 1166-71.
Fitton et al., *J. Organometallic Chem.*, 28 (1971), 287-91.
Ishii et al., *J. Organometallic Chem.*, 73 (1974), 411-18.
Koketsu et al., Chubu Kogyo Daigaka, Kiyo, A. 16A, 103-9 (1980).
Johnson, et al., *J. Chem Soc.*, (1974), 34-40.
Tolman, *Chemical Reviews*, 1977, vol. 77, No. 3, 313-48.
Heck et al., *Catalysis in Organic Synthesis*, Patel, 1978, 7th Ed. 195-218.
"Chelate-Assisted, Pd-Catalyzed Efficient Carbonylation of Aryl Chlorides" by Y. Ben-David, M. Portnoy and D. Milstein, *J. Am. Chem. Soc.* 1989 111, p. 8742-8744.
"Oxidative Addition of Water to the Ru$^{11}$ Catalyst K[Ru$^{11}$(Hedta)CO)]: Homogeneous Catalysis of the Water-Gas Shift Reaction under Ambient Conditions."
"Palladium-Catalyzed Amidation of Aryl, Heterocyclic, and Vinylic Halides", by A. Schoenberg and R. F. Heck *J. Org. Chem.* vol. 39, No. 23, 1974 pp. 3327-3331.
"Amidation of Chloroalkenes Catalyzed by Tertiary Phosphine Complexes of Palladium (0)" by Paul P. Nicholas, *J. Org. Chem.* vol. 52, No. 23, 1987 pp. 5266-5272.

*Primary Examiner*—Carolyn Elmore
*Attorney, Agent, or Firm*—Alfred D. Lobo; Nestor W. Shust

[57] ABSTRACT

A unique two-step process is disclosed for the surprisingly high rate of amidation of vinyl chloride (VCl) with carbon monoxide and certain amines catalyzed by an effective amount of monodentate tertiary phosphonium complexes of Pd(0). The rate is orders of magnitude faster than that of other monochloroalkenes. When compared with the three chloropropenes, the simplest alkyl-substituted derivatives of VCl, rates differ by a factor of about 40 to 70 with ammonia as the amine. The reaction product with VCl is mainly the Michael adduct of the amine with the acrylamide produced. However, the chloroprenes give the propenamides with retention of configuration in the case of cis- and trans-1-chloropropene, and no adduct formation. The formation of this adduct has an important influence on catalyst stability since it can compete with the addition of the tertiaryphosphonium ligand from the catalyst complex. The latter reaction produces small amounts of a phosphonium chloride, and the resulting loss of ligand causes palladium metal to separate, thereby deactivating the catalyst. This understanding enables one to choose the best ligand/amine combination to suppress this catalyst deactivation mechanism. Triphenylphosphine and dimethylamine is a particularly effective combination.

5 Claims, 1 Drawing Sheet

PROCESS FOR THE PALLADIUM-CATALYZED AMIDATION OF VINYL CHLORIDE

CROSS REFERENCE TO RELATED APPLICATION

This application is a continuation-in-part application of Ser. No. 683,840 filed Dec. 19, 1984, abandoned.

BACKGROUND OF THE INVENTION

This invention relates to a process for the amidation of vinyl chloride (VCl), and the discovery of a surprising difference in the rate of this amidation compared with that of structurally similar vinylic chlorides when a zero valent monodentate palladium catalyst is used under certain conditions which unexpectedly also provide the catalyst with very long life. Amidation refers to the known reaction of an amine with carbon monoxide, under elevated temperature and pressure, to produce an amide. The commercial promise of amidation reactions with known catalysts has never materialized. Among the main reasons is the discouragingly low reaction rates with all but the organo-bromides and organoiodides which are of little commercial significance. Thus, over the years, those skilled in the art had a well-established experimental basis for eschewing further investigation of amidation applied to chloroalkenes and chloroarenes.

The particular promise of the amidation of VCl is based on the unexpectedly high rate of the rate-controlling oxidative addition step which leads to the nearly quantitative formation of the Michael adduct (formed by a Michael addition) of the amine reactant with the acrylamide or N-substituted acrylamide produced (both referred to hereinafter as "acrylamides" for brevity). This Michael adduct formation occurs only with VCl and no other chloroalkene, with unexpectedly high selectivity while maintaining excellent catalyst performance, combined with extended catalyst life, though the catalyst is a known palladium catalyst. This process affords a practical route to the manufacture of acrylamide, N-phenylmethacrylamide, and N,N-dimethylacrylamide, each of which is useful in a wide array of polymers. Dimethylamine in particular provides greatly enhanced catalyst stability, because of its ability to overcome the causes of deactivation which I have identified.

More specifically this invention relates to the use of known monodentate tertiary-phosphine complexes of palladium(0), such as tetrakis(triphenylphosphine)palladium, per se, or generated in situ, which are far more effective than other palladium catalysts, or Group VIII catalysts, in the amidation of VCl with ammonia and CO; and with certain primary and secondary amines, all of which form the Michael adduct. The Michael adduct, derived from the addition of amine to the acrylamide produced is then conveniently and efficiently converted to the desired acrylamide.

This amidation process involves a series of reactions in which the key step is the oxidative addition of Pd(0) to the organohalide. It is well-known that oxidative addition occurs far more rapidly with bromides and iodides than with chlorides. In the art, the only example of a monochloroalkene undergoing amidation to an alpha-beta unsaturated amide is that of 2-chloropropene disclosed in U.S. Pat. Nos. 3,988,358 and 4,128,554 to Heck. A carbonylation reaction, only superficially analogous to the foregoing Heck amidation, and presumably therefore, not cited in Heck's '554 patent, is the process disclosed in U.S. Pat. No. 3,991,101 to Knifton. Knifton provides a specific illustration of carbonylation of VCl itself. In part A of Example 1, he uses $Pd(PPh_3)Cl_2$, the same Pd(II) catalyst used by Heck, together with stannous chloride co-catalyst for the carbonylation in methanol to produce methyl acrylate in 83% yield. But in part B, the same $Pd(PPh_3)C_2$ catalyst, but with no stannous chloride, result in a different product. He found that "the major reaction is CO addition to the carbon-carbon double bond and that the major portion by far is methyl alpha-chloropropionate (selectivity %-74), with approximately one quarter ($\frac{1}{4}$) as much of the desired methyl acrylate being formed (selectivity %-18) plus a significant quantity of dimethyl alpha-methyl malonate (selectivity %-8)". In other words, the main product is the saturated ester resulting from addition to the double bond rather than substitution of chlorine.

Generally, carbonylation reactions of halogen-substituted unsaturated compounds, are well known. But the reactions are also well known for their differences in rates and selectivity. These differences can depend upon whether the compound is an allylic, aryl or a vinyl halide, and as illustrated by Heck, also on the type of halide, e.g. bromides and iodides which do not require the forcing conditions of vinylic chlorides because the latter are so unreactive.

The surprisingly high rates obtained with aryl and vinylic halides as compared with analogous palladium-catalyzed reactions with allylic halides was the basis of the Heck '358 and '554 inventions. In the parent '358 reference he states that his object is "to produce carboxylic esters and amides in good yields under mild conditions from organic halides other than allylic halides, including those organic halides that have been considered to be unreactive as compared to allylic halides." (see col 1, lines 21-26, emphasis supplied).

Consistent with this objective, Heck's investigation of the amidation reaction was generally limited to atmospheric pressure and a temperature in the range from 60°-100° C. (see first line of "Results and Discussion" of the article titled "Palladium-Catalyzed Amidation of Aryl, Heterocyclic, and Vinylic Halides" by A. Schoenberg and R.F. Heck, 39 *Jour. Org. Chem.*, p 3327 (1974)) and examples in the '358 and '554 patents. However, the rea of 2-chloropropene with CO and aniline in the presence of a stoichiometric quantity of tri-n-butylamine was at 135° C. to 140° C. and pressure of about 800 psig for periods of 12 to 24 hr (see example 33 of '358 patent, example 13 of the '554 patent, and experimental section of the article, pg 3330). With further reference to rates, note that the Heck disclosure is related to any non-allylic halide, specifically covering chlorides, bromides and iodides without suggesting that there may be any distinguishing characteristics in the reactivity of one halide over the other, that would be critically important to their commercial importance.

That there should be a notable difference in the rates obtained with various non-allylic halides is expected. This is especially true when comparing bromides and iodides with chlorides and fluorides. The difference in rates between chlorides on the one hand, and bromides and iodides on the other, is confirmed by comparing rough estimates of rates calculated from Heck's examples. These are estimates because the Heck experiments with 2-chloro-propene were directed to determining yields, not rates—the stated object to the contrary. His experiments were carried out to unspecified high conversions of aniline, the limiting reagent. Therefore, when comparing rates of product formation among the bromides, iodides, and 2-chloropropene, one must assume that the reported reaction times correspond to the time required to reach roughly the same aniline conversion. Such a comparison shows a substantially slower rate for 2-chloropropene despite more vigorous conditions. To avoid this ambiguity, I have measured and compared rates of all three chloropropenes with VCl under the same conditions.

In my experiments I have measured the continuous disappearance of amine with time and expressed this as "turnover rate". The turnover rate used herein is defined as:

(moles of reactant converted) divided by (moles of catalyst) for each hour of reaction time. This form of measurement of rate is routinely used in the art (see for example "Catalysis and Inhibition of Chemical Reactions", by P.G. Ashmore, pp 9, Butterworths, London, 1963).

In the illustrative examples I have presented for VCl amidation, I have reported the rate of disappearance of ammonia used to convert VCl simply because this rate can be measured continuously by gas chromatography. However, when I compared the amidation of VCl with the three chloropropenes, the latter reactions were so slow that the rate of disappearance of ammonia could not be measured accurately. In this case, it is far more accurate to measure the formation of chloride ion as $NH_4Cl$ by titration, which I did, and reported the relative rates (see example 8 herein).

The rates in the Heck references may be compared with those I obtained if they are converted to "turnover rate" with the appropriate assumptions. Despite the high cost of catalyst and the economics of rates, Heck's reports of his results focused more on yield than on catalyst longevity or rates.

It is well recognized in the art that the oxidation addition step which activates the carbon-halogen bond in this process is very slow for vinyl or aromatic carbon-X bonds when X is Cl, compared with Br or I. Therefore bromides and iodides are usually used when this activation, step is required in a chemical process. Thus, lactams are prepared from bromoalkenes and iodoalkenes having secondary substituents. See M. Mori, et al *Jour. Org. Chem.* 48 p 4058 (1983). Benzolactams are prepared from o-bromoamino-alkylbenzene by photochemical carbonylation under phase transfer conditions using cobalt carbonyl as the catalyst. See J. Brunet, et al *Jour. Org. Chem.* 48 p 1166 (1983). All but one of the many examples in the Heck references relate to bromides and iodides. The resistance of chloroalkyls, monochloroalkenes and chloroarenes toward oxidation addition with zero-valent Ni, Pd and Pt complexes is well documented. See P. Fitton, et al *Jour. Organometallic Chem.* 28 p 287 (1971); J.T. Colman, et al *Principles and Applications of Organotransition Metal Chemistry* p 185 (1980); and, R.F. Heck, et al *Catalysis in Organic Synthesis* 7th ed. p 195-218, inter alia.

The presence of the methyl group in 2-chloropropene is the reason for the low reaction rate. Moreover, it suppresses formation of the Michael adduct derived from addition of amine with the acrylamide produced. Reactivity is greatly enhanced when the monochloroalkene is unsubstituted, that is, VCl. Heck did not discover that VCl would give the high reaction rate and form the Michael adduct. Though he includes VBr in his broad disclosure of useful reactants, there is nothing in his disclosure to suggest that VBr may behave differently from the host of other compounds since there is no mention anywhere, of the Michael adduct. Not having run VBr or VCl, he could not know that the formation of the Michael adduct depends upon the unique unsubstituted character of VCl or VBr, and that it has an important influence on catalyst stability. The Michael adduct is critical to catalyst stability because it suppresses formation of the phosphonium chloride which removes stabilizing ligand from the metal in the complex, thus causing the metal to separate.

Moreover, Heck added a stoichiometric amount of tri-n-butylamine to remove HCl when a weakly basic amine is amidated. The presence of a basic tertiary amine in a molar equivalent amount compared to the weakly basic amine, or in excess of that amount, was claimed to be a necessary condition to enable one to carry out the Heck invention in most instances. It is unnecessary in VCl.

Still another difference that I have observed relates to the role of the amine as the reducing agent for the catalyst complex. In every Heck example, the catalyst used was a $Pd^{2+}$ complex (e.g. $Pd(PPh_3)_2)Cl_2$) which was undoubtedly reduced to the active $Pd(0)$ complex in situ. I have found that the amine is the principal reducing agent for this process, at least with VCl, and that a suitable amine is one that contains alkyl substituents having alpha hydrogen atoms. Thus, while either $Pd(PPh_3)_2)Cl_2 + 2PPh_3$ or $Pd(PPh)_4$ are equivalent catalysts when dimethylamine is the amine reactant, they are not equivalent when using ammonia. $Pd(PPh_3)_2Cl_2$ is essentially inactive in VCl amidation with ammonia as shown in example 7 herein; therefore Heck's disclosure relating to the amidation of VCl with the catalyst he used, is not an enabling disclosure. The choice of amine can be an important factor in obtaining catalyst longevity, depending upon the extent to which $Pd(PR_3)_2Cl_2$, defined herebelow, forms during amidation.

Had Heck run the reaction with VCl instead of 2-chloropropenes, he would have observed its high reactivity, the formation of the Michael adduct, its importance to catalyst stability, and reported the results.

SUMMARY OF THE INVENTION

It has been discovered that vinyl chloride (VCl) is unique in that its rate of amidation with carbon monoxide and certain amines catalyzed by an effective amount of monodentate tertiary phosphonium complexes of $Pd(0)$ is orders of magnitude faster than that of other monochloroalkenes. When compared with the three chloropropenes, the simplest alkyl-substituted derivatives of VCl, rates differ by a factor of about 40 to 70 with ammonia as the amine. The reaction product with VCl is mainly the Michael adduct of the amine with the acrylamide produced. However, the chloroprenes give the propenamides with retention of configuration in the case of cis- and trans-1-chloropropenes, and no adduct formation. The formation of this adduct has an important influence on catalyst stability since it can compete with the addition of the tertiary-phosphonium ligand from the catalyst complex. The latter reaction produces small amounts of a phosphonium chloride, and the resulting loss of ligand causes palladium metal to separte, thereby deactivating the catalyst. This understanding enables one to choose the best ligand/amine combination to suppress this catalyst deactivation mechanism.

Triphenylphosphine and dimethylamine is a particularly effective combination.

It is therefore a general object of this invention to provide a two step process wherein the Michael adduct is formed in the first step, and then, in the second step, is thermally reversed to the corresponding acrylamide and amine.

It has still further been discovered that the amidation of VCl with CO and primary amines is surprisingly constant, even through high conversions, though the reaction is not zero order in amine (the rate changes with the amount of amine initially charged).

DETAILED DESCRIPTION OF PREFERRED EMBODIMENTS

Figure 1:
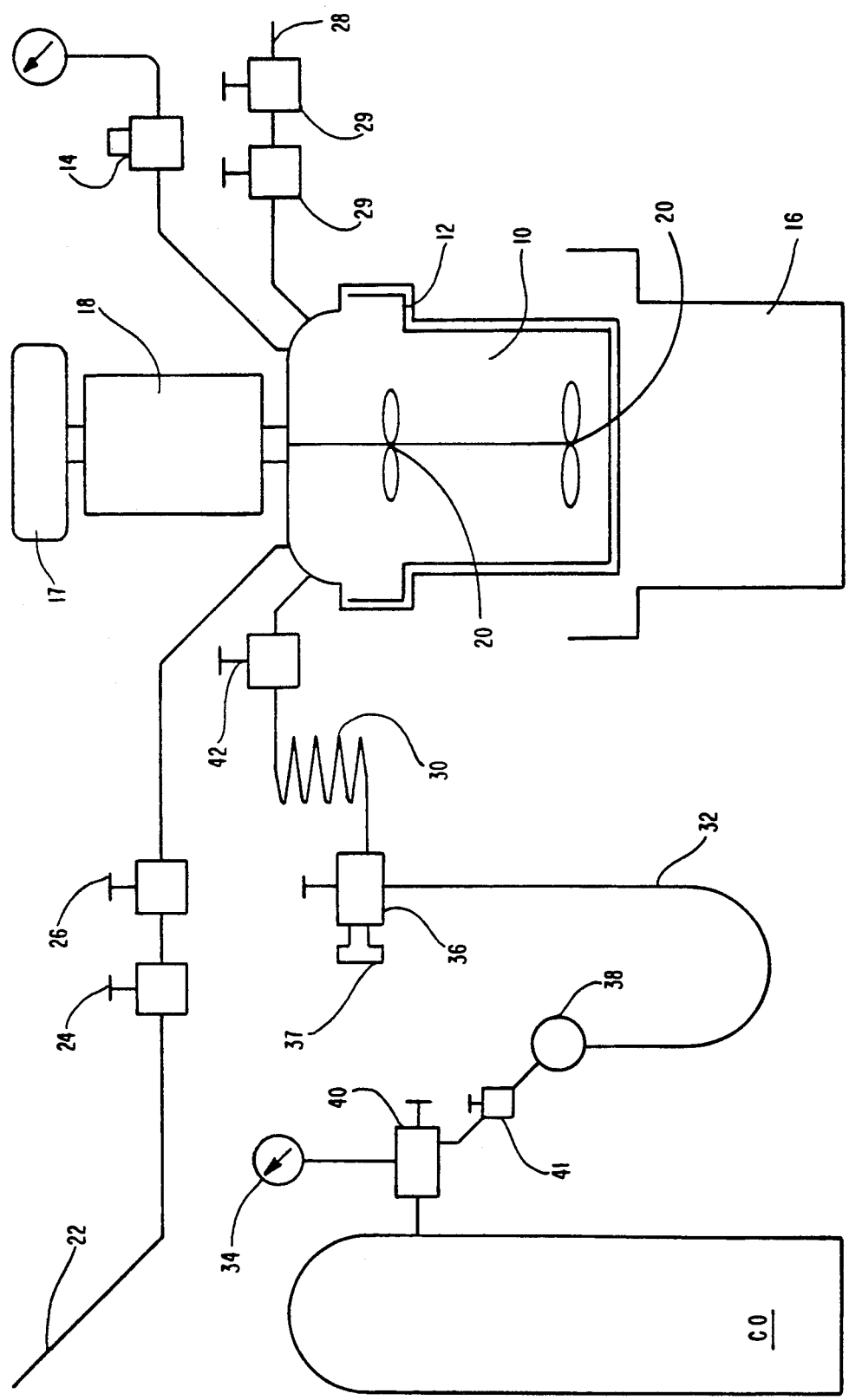
FIG. 1 is a schematic representation of a reactor with accessories, adapted to practice the process of this invention.

The preferred embodiment of this invention relates to amidation of vinyl chloride in a two-step process comprising, in a first step, reacting vinyl chloride and carbon monoxide with ammonia or a primary or secondary amine in the presence of a catalytically efective amount of a palladium(0) triorganophosphine complex, either charged as such or produced in situ under the reaction conditions.

The reaction proceeds in the absence of a tertiary amine at a temperature from above about 80° C. to below a temperature at which the Michael adduct dissociates to the corresponding acrylamide. The pressure is superatmospheric being in the range from above about 200 psig but below 600 psig. Formation of the adduct from the amine and the amide formed during the reaction is a specific condition which enhances catalyst longevity by suppressing the addition of phosphine ligand with which it competes. Thus, the combination of a highly nucleophilic amine and a moderately nucleophilic triorganophosphine ligand leads to high catalyst stability. A particularly effective combination is dimethylamine with the ligand being triphenylphosphine.

Additional details of the process, relevant comparisons of reactions with other chloroalkenes, and the manner of identification of intermediates and products of the reaction, are set forth in my article titled "Amidation of Chloroalkenes Catalyzed by Tertiary Phosphine Complexes of Palladium (0)"in *J. Org. Chem.* 52 pp 5266-5272 (1987), the disclosure of which is incorporated by reference thereto as if fully set forth herein.

It will be evident that the term "acrylamide" is used herein in a general sense to refer to substituted acrylamides such as are formed with amines having specified N-substituents, as well as acrylamide. The manufacture of such acrylamides by amidation is effected by a catalytic reaction utilizing a monodentate triorganophosphine complex of palladium(0) catalyst having the stoichiometry:

$$Rd(PR_3)_n$$

wherein

R represents $C_1$-$C_4$ lower alkyl, phenyl, $C_1$-$C_4$ alkylphenyl, and cycloalkyl having 4 to 6 ring carbon atoms; and, n is an integer in the range from 2 to 6.

When n>4, excess ligand is charged. Thus, an authentic Pd(0) complex, e.g. Pd(PPh$_3$)$_4$, may be used with or without added ligand, or it may be generated in situ from the Pd(0) complex, Pd$_3$(TBAA)$_3$CHCl$_3$ (where TBAA is an acronym for tribenzylidene acetylacetone) as described by Ishi, Y., et al, in *J. Organomet. Chem.* 73 pp 411 (1974), with the required amount of phosphine ligand to obtain the desired stoichiometry. Alternatively, a Pd(II) complex may be used, e.g. Pd(PR$_3$)$_2$X$_2$, where X = halogen, if the amine contains an alpha hydrogen, the amine thereby also serving as a reducing agent to produce the active Pd(0) complex. Additional ligand may be used with Pd(PR$_3$)$_2$X$_2$ in whatever stoichiometry desired. Thus, this latter approach will be unsuitable with ammonia since it is incapable of effecting the reduction.

The desired overall amidation reaction is represented as follows:

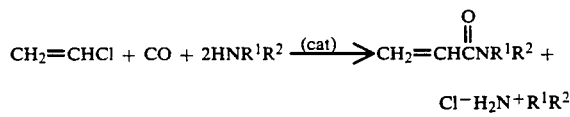

$$Cl^-H_2N^+R^1R^2$$

wherein $R^1$ and $R^2$ independently represent H, $C_1$-$C_4$ lower alkyl, phenyl, and $C_1$-$C_4$ alkylphenyl, provided both $R^1$ and $R^2$ are not phenyl or $C_1$-$C_4$ alkylphenyl. Amines with alkyl substituents having more than 4 carbon atoms, do not provide high rates of formation of the Michael adduct. Thus, not only is the choice of the monochloroalkene critical, but also the choice of the amine.

The ideal reaction proceeds stepwise, as is represented for ammonia, as follows:

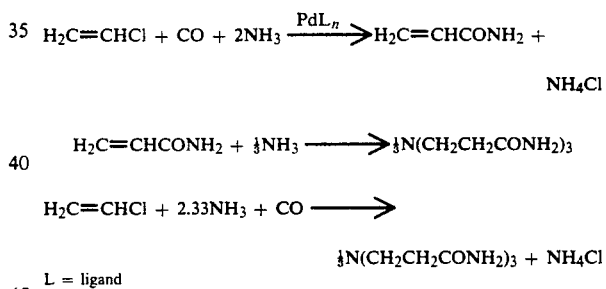

L = ligand

The reaction products are identified as nitrilotripropanamide, acrylamide, and ammonium chloride. In practice, a very small amount of nitrilotripropanamide hydrochloride, ClHN(H$_2$C=CHCONH$_2$)$_3$, is formed, as well as some acrylamide, depending upon reaction conditions. Also formed are very small amounts of (2-carbamoylethyl)triphenylphosphonium chloride (ClPh$_3$PCH$_2$CH$_2$CONH$_2$), the adduct from the catalyst ligand.

In an analogous manner, dimethylamine gives the Michael adduct (CH$_3$)$_2$NCH$_2$CH$_2$CON(CH$_3$)$_2$ and the corresponding amine hydrochloride; and, aniline gives the Michael adduct PhHNCH$_2$CH$_2$CONHPh and the corresponding amine hydrochloride.

The Michael adducts are preferably heated under reduced pressure to a temperature in the range from about 160° C. to about 200° C. to yield the corresponding acryl-amides.

The deactivation of Pd(PPh$_3$)$_4$ usually occurs within a few hundred turnovers (number of moles of VCl converted, divided by number of moles of catalyst) during amidation with ammonia. This is accompanied by the formation of the phosphonium salt and colloidal metallic palladium. The consumption of tertiary phosphine in this way causes palladium to cluster and precipitate. Though catalyst life can be extended with increasing $PPh_3/Pd$ ratios, dectivation eventually occurs. Accordingly, complexes of more nucleophilic tertiary phosphines deactivate faster and form phosphonium salt more rapidly. When catalyst activity is prolonged with increased $PPh_3/Pd$ ratios, small amounts of $Pd(PPh_3)_2Cl_2$ and 1,3-butadiene are detected among the products Therefore this slow reaction is also able to make a measurable contribution toward deactivation during amidation with ammonia.

For the above reasons, the type of amine used in VCl amidation can have a major influence on catalytic stability. Dimethylamine, for example, affords far greater catalyst stability than ammonia, stemming from its ability to overcome the two identified causes of deactivation. First, the Michael addition of dimethylamine to N,N-dimethyl-acrylamide occurs much faster than phosphonium salt formation. Secondly, unlike ammonia, dimethylamine is able to rapidly reduce $Pd(PPh_3)_2Cl_2$ to the active catalyst, such that $Pd(PPh_3)_2Cl_2 + 2PPh_3$ is catalytically equivalent to $Pd(PPh_3)_4$. Thus to the extent that some coupling occurs and produces $Pd(PPh_3)_2Cl_2$, it is not a damaging side reaction with dimethylamine as it is with ammonia. Thus, more than 1000 turnovers (moles of dimethylamine per mole of catalyst)have been achieved with dimethylamine without catalyst deactivation.

The process of the invention may be practiced in the apparatus schematically illustrated in FIG. 1, wherein a 500 ml stainless steel reactor, identified generally by reference numeral 10, commercially available from Autoclave Engineers as a Zipperclave reactor, is provided with a glass liner 12 and rupture disc 14. The reactor is placed in a thermostated mantle 16 which provides accurate control of temperature within the reactor. An air motor 17 drives an agitator 18 provided with paddles 20 to mix the contents of the reactor. A vacuum line 22 provided with a metering cock and a stop cock allow subatmospheric pressure control of reactor pressure. Also provided are a sampling line 28 including block valves 29, an inlet line 30 including a U-tube 32, a pressure gauge 34, a three-way cock 36, a port 37 for introducing gases, a metering valve 38, a carbon monoxide inlet cock 40 and block valves 41, 42.

EXAMPLE 1

Preparation of catalyst:

A 100 ml 3-neck flask is fitted with an inert gas inlet, a thermometer, a gas bubbler, a magnetic stirring bar, and a port including a rubber septum. The flask is purged with nitrogen and charged with 60 ml of DMSO, 6.5 g (0.025 moles) of triphenylphosphine, and 0.885 g (5 millimoles) of palladium chloride. Under agitation in an inert atmosphere, here argon, the mixture is heated to 140° C. to produce a solution. The mixture is then allowed to cool slowly while being agitated. At 130° C., 1.8 g (0.020 moles) of 85% hydrazine hydrate is added employing a syringe over approximately 2 min. After cooling, crystallized product is filtered through a coarse sintered glass disc under nitrogen and washed twice with 10 ml aliquots of ethanol followed by pentane washes. The crystals are dried with nitrogen at room temperature to yield 5.43 g (4.70 millimoles) of yellow crystals with 94% yield. The resulting tetrakis(triphenylphosphine)palladium is employed to illustrate the process of this invention.

EXAMPLE 2

In a typical acrylamide reaction, the reactor 10 having a glass liner 12 was charged 0.36 moles tetrakis(triphenylphosphine)palladium catalyst and evacuated to less than 26 Pa employing the line 22. The reactor 10 was immersed in an ice bath; 63.4 grams (1.01 moles) vinyl chloride was condensed into the reactor by vapor transfer. The catalyst-VCM mixture was agitated while venting 800 ml of VCM vapor employing the line 28 as a purge leaving 61.4 grams (0.983 moles) of VCl in the reactor. The reactor was placed in the mantle 16. The U-tube 32 was evacuated, cooled in liquid nitrogen, and the three way cock 36 was opened to condense the amine, here ammonia, into the U-tube. The three way valve 36 was adjusted to permit flow from the U-tube 32 to the valve 42, and as the U-tube was warmed with hot tap water, the valve 42 was opened to admit the ammonia into the reactor 10. The reactor 10 was then rapidly pressurized with carbon monoxide with the agitator 18 idle through the valves 40, 41, 36, 42 and the U-tube 32. The partial pressure of carbon monoxide as noted herein is the difference between pressure in the reactor 10 immediately before and after introduction of carbon monoxide and before any heating or agitation. The reactor was heated to 100° C. while stirred. Based upon known vapor pressure and density data, it was believed that about 53 milliliters of VCM remained in the liquid state after heating. Ammonia disappearance was monitered by gas chromotography employing a $0.32 cm \times 183 cm$ silanized column packed with 80/100 mesh Poropak PS operated at 60° C. VCM was the internal standard. The sample was the piping volume between the valves 29 in the line 28 which was maintained at 120° C. At the conclusion of the reaction, the mantle was removed and the reactor 10 was cooled in ice water. After venting (while stirred) and opening the reactor, the contents thereof were extracted with 50–100 milliters of $D_2O$ and the resulting solution filtered. The weight of the combined extract was determined and teriary-butanol was added as an internal reference for quantitative $^1H$ NMR analysis. VCl conversions were determined by potentiometric titration for chloride using silver nitrate (aqueous) and a chloride specific electrode. Reported yields are based upon these chloride titrations.

This Example was repeated varying the quantities of ammonia, carbon monoxide, and catalyst included in the reactor. The results are set forth in Table I wherein R in the catalyst is a phenyl group. The initial rate of ammonia consumption is the value reported in Table 1.

As will be seen from Table 1, the amount of amine charged ranges from 0.074 mol to 0.36 mol and the amount of catalyst ranged from 0.36 mmol to 0.72 mmol. The amount of amine charged will depend upon the particular characteristics of the amine. Rate decreases with increasing concentration for ammonia, but rate increases with increasing concentration for dimethylamine. The preferred range of amine charged will generally range from about 0.01 mol to about 1.0 mol for 0.36 mmol of catalyst.

The initial rate of reaction is reported because the rate for reaction is approximately a straight line and it is limited by the amount of amine present. Calculation of the turnover rate from the fifth entry of Table 1, gives 93 hr$^{-1}$. For ammonia, the turnover rate ranges from about 50 hr$^{-1}$ to about 500 hr$^{-1}$.

TABLE I

Influence of Reaction Variables on VCl Amidation

| $P_{(CO)}$ (psi) | $NH_3$ (mol) | T (°C.) | RATE($NH_3$) (mol min$^{-1}$) × 10$^4$ | Pd(PR$_3$*)$_4$ (mmol) | YIELD (%)$^a$ d | e | f | g | g, % of$^b$ THEOR. MAX | COMBINED YIELD (%) | N. BAL$^c$ (%) | VCl CONVER. (mmol) | RECHARGE $NH_3$ | REACTION TIME (min) |
|---|---|---|---|---|---|---|---|---|---|---|---|---|---|---|
| 240 | .35 | 100 | 5.3 | .36 | 81 | 16 | .24 | .04 | 1.4 | 96 | 109 | 49.8 | NO | 316 |
| 240 | .36 | 100 | 4.7 | .36 | 70 | 17 | 2.2 | .04 | 1.4 | 88 | 105 | 49.5 | NO | 221 |
| 240 | .20 | 100 | 5.9 | .36 | 87 | 11 | 2.7 | .8 | 56. | 101 | 105 | 77.9 | NO | 484 |
| 240 | .16 | 100 | 10. | .36 | 77 | 15 | 2.0 | .6 | 40. | 94 | 86 | 75.1 | YES | 341 |
| 240 | .12 | 100 | 13. | .36 | — | — | — | — | — | — | — | 50.6 | NO | 110 |
| 240 | .12 | 100 | 15. | .36 | — | — | — | — | — | — | — | — | NO | — |
| 240 | .074 | 100 | 16. | .36 | 0 | 16 | 66 | 5.7 | 100. | 88 | 80 | 27.9 | NO | 42 |
| 240 | .12 | 100 | 14. | .36 | with .034 mol d added | | | | — | — | — | — | NO | 85 |
| 320 | .12 | 100 | 6.8 | .36 | 79 | 13 | 5.3 | .9 | 49. | 102 | 93 | 81.4 | YES | 396 |
| 160 | .12 | 100 | 18. | .36 | 72 | 20 | 1.4 | 1.2 | 84. | 95 | 106 | 124. | YES | 433 |
| 120 | .13 | 100 | 18. | .36 | 40 | 10 | 31. | 3.2 | 100. | 85 | 84 | 53.4 | NO | 70 |
| 80 | .15 | 100 | 12. | .36 | 61 | 8 | 17. | 2.1 | 65. | 89 | 89 | 44.5 | NO | 102 |
| 160 | .12 | 90 | 4.1 | .36 | 71 | 10 | 3.3 | .7 | 28. | 86 | 86 | 56.8 | YES | 598 |
| 160 | .12 | 110 | 25. | .36 | 55 | 33 | .8 | 1.3 | 51. | 90 | 77 | 55.1 | YES | 211 |
| 160 | .18 | 100 | 12. | .36 | 77 | 17 | 2.2 | .7 | 34. | 97 | 85 | 70.9 | YES (f = .5) | 294 |
| 160 | .18 | 100 | 13. | .36 | 66 | 14 | 1.6 | 1.1 | 60. | 83 | 84 | 76.9 | YES (f = 0) | 285 |
| 160 | .18 | 100 | 39. | .72 | 64 | 26 | nil | 1.2 | 62. | 92 | 84 | 150. | YES | 650 |

$^a$Based on VCl converted
$^b$Theoretical maximum is PPh$_3$ available from Pd(PPh$_3$)$_4$
$^c$Nitrogen in products ÷ ammonia consumption (gc)
$^d$N(CH$_2$CH$_2$CONH$_2$)$_3$
$^e$Cl$^-$HN(CH$_2$CH$_2$CONH$_2$)$_3$
$^f$acrylamide
$^g$Cl$^-$R$_3$PCH$_2$CH$_2$CONH$_2$
*R is phenyl

EXAMPLE 3

Example 2 was repeated employing para-substituted phenyl groups in lieu of unsubstituted phenyl in the triphenylphosphine liqand of the catalyst. The results are set forth in Table II.

EXAMPLE 4

Example 2 was repeated employing alternate catalyst ligands wherein Pd(PR$_3$)n was generated in situ from Pd$_3$(TBAA)$_3$CHCl$_3$ with a variety of phosphorous containing ligands, that is PR$_3$, and a tertiary-silbene added in the stoichiometry indicated. The results are set forth in Table III wherein Ph represents phenyl.

TABLE II

Para-Substituent Effect on Amidation

| $P_{(CO)}$ (psi) | $NH_3$ (mol) | T (°C.) | Rate ($NH_3$) (mol min$^{-1}$) × 10$^4$ | R for Pd(PR$_3$)$_n$ R | n$^g$ | (mmol) | YIELD (%) a | b | c | d | d, % of Total Theor. max | N Yield (%) | N Bal. (%) | VCl Conver. (mmol) | Recharge Ammonia | React. Time (min) |
|---|---|---|---|---|---|---|---|---|---|---|---|---|---|---|---|---|
| 240 | .12 | 100 | 7.6 | para-C$_6$H$_4$CF$_3$ | 4 | .36 | 51 | 12 | 3. | .6$^f$ | 7$^f$ | 67 | 59 | 15.7 | no | 208 |
| 240 | .12 | 100 | 8.6 | para-C$_6$H$_4$F | 4 | .36 | 72 | 9.3 | 0 | 0 | 0 | 81 | 54 | 36.5 | yes | 275 |
| 240 | .12 | 100 | 13.$^e$ | C$_6$H$_5$ | 4 | .36 | 82 | 7.3 | 1.6 | 1.0 | 47 | 92 | 81 | 64.5 | yes | 350 |
| 240 | .12 | 100 | 27. | para-C$_6$H$_4$CH$_3$ | 4 | .36 | 63 | 22. | 0 | 2.9 | 90 | 88 | 66 | 45.2 | yes | 95 |

$^a$N(CH$_2$CH$_2$CONH$_2$)$_3$
$^b$Cl$^-$HN(CH$_2$CH$_2$CONH$_2$)$_3$
$^c$acrylamide

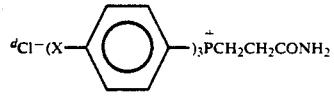
$^d$Cl$^-$(X—⬡—)$_3$PCH$_2$CH$_2$CONH$_2$ $^e$Average of three runs.
$^f$Upper limit.
$^g$from Pd(PR$_3$)$_3$ and one equivalent of PR$_3$

TABLE III

Amidation Catalyzed by PdLn Generated in-situ From Pd$_3$(TBAA)$_3$(CHCl$_3$) and L

| $P_{(CO)}$ (psi) | $NH_3$ (mol) | T (°C.) | Rate (mol min$^{-1}$) × 10$^4$ | Pd(PR$_3$)$_n$ PR$_3$ | n | (mmol) | YIELD (%)$^a$ a | b | c | d | d, % of Total Theor. max | N Yield (%) | N Bal. (%) | VCl Conver. (mmol) | Recharge Ammonia | React. Time (min) |
|---|---|---|---|---|---|---|---|---|---|---|---|---|---|---|---|---|
| 240 | .12 | 100 | 14 | PPh$_3$$^f$ | 4 | .36 | 68 | 13 | 2.8 | .9 | 35 | 85 | 70 | 57.2 | yes | 180 |

TABLE III-continued

Amidation Catalyzed by PdLn Generated in-situ From Pd₃(TBAA)₃(CHCl₃) and L

| $P_{(CO)}$ (psi) | $NH_3$ (mol) | T (°C.) | Rate (mol min$^{-1}$) × 10$^4$ | Pd(PR$_3$)$_n$ PR$_3$ | n | (mmol) | YIELD (%)$^a$ a | b | c | d | d, % of Total Theor. max | N Yield (%) | N Bal. (%) | VCl Conver. (mmol) | Recharge Ammonia | React. Time (min) |
|---|---|---|---|---|---|---|---|---|---|---|---|---|---|---|---|---|
| 240 | .12 | 100 | 0.1 | P(o-tolyl)$_3$ | 2 | .36 | — | — | — | — | — | — | — | .8 | no | 134 |
| 240 | .12 | 100 | 0.05 | Ph$_2$PCH$_2$CH$_2$PPh$_2$ | 2 | .36 | — | — | — | — | — | — | — | .4 | no | 171 |
| 240 | .12 | 100 | 0.05 | ortho-(PPh$_2$)$_2$C$_6$H$_4$ | 2 | .36 | — | — | — | — | — | — | — | .5 | no | 257 |
| 240 | .12 | 100 | 37$^e$ | P(cyclohexyl)$_3$ | 4 | .36 | 14 | 3.2 | 63. | — | — | 80 | 76 | 50. | no | 190 |
| 240 | .12 | 100 | 71 | P(cyclohexyl)$_3$ | 2 | .36 | 63 | 12. | 3. | — | — | 69 | 69 | 92.9 | yes | 228 |
| 240 | .12 | 80 | 8.8 | P(cyclohexyl)$_3$ | 2 | .36 | — | — | — | — | — | — | — | 57.5 | yes | 305 |
| 240 | .12 | 100 | 0 | Sb(p-toluene)$_3$$^g$ | 4 | .36 | — | — | — | — | — | — | — | 0 | no | 200 |
| 240 | .12 | 100 | 0.02 | P(OPh)$_3$ | 2 | .36 | — | — | — | — | — | — | — | 1.8 | no | 225 |
| 240 | .12 | 100 | 28 | PPh$_3$ | 2 | .36 | — | — | — | — | — | — | — | — | — | — |
| 240 | .12 | 100 | 0.1 | P(1-napthyl)$_3$ | 4 | .36 | — | — | — | — | — | — | — | 1.1 | no | 250 |
| 240 | .12 | 90 | 43 | P(tertiary-butyl)$_3$ | 4 | .36 | 31 | 4.4 | 48. | 4.7 | 100 | — | — | 38.2 | no | 126 |

$^a$N(CH$_2$CH$_2$CONH$_2$)$_3$
$^b$Cl$^-$ $\overset{+}{N}$H(CH$_2$CH$_2$CONH$_2$)$_3$
$^c$acrylamide
$^d$Cl$^-$(R$_3$)$\overset{+}{P}$CH$_2$CH$_2$CONH$_2$
$^e$170 min induction period followed by fast reaction
$^f$Ph is phenyl
$^g$Sb substitutes for P

EXAMPLE 5

Example 2 was repeated employing aniline and dimetylamine in lieu of ammonia. The results are set forth in Table IV.

Calculation of the turnover rate for the first entry in Table IV gives 650 hr$^{-1}$ for dimethylamine, and for As has been stated hereinabove, the preferred concentration for the formation of the Michael adduct, in a major molar amount relative to the corresponding acrylamide, will depend upon the choice of amine. Whichever amine chosen, the required concentration of amine to be used will therefore be such that a major molar amount of the Michael adduct is formed.

TABLE IV

VCl Amidation with Dimethylamine and Aniline

| $P_{(CO)}$ | Amine (mol) | T(°C.) | Rate (mol min$^{-1}$) × 10$^4$ | Pd(PPh$_3$)$_4$ (mmol) | Yield (%) d | d · HCl | e | f | VCl Conver. (mmol) | Recharge Amine | React. Time (min) |
|---|---|---|---|---|---|---|---|---|---|---|---|
| 240 | Dimethylamine (.12) | 100 | 39 | .36 | — | 94 | — | 0 | 158 | yes | 44 |
| 240 | Dimethylamine (.12) | 90 | 14 | .36 | 100$^a$ | — | — | 0 | 41.6 | no | 86 |
| 240 | Dimethylamine (.12) | 90 | 14 | .36 | — | — | — | — | — | — | — |
| 240 | Dimethylamine (.059) | 90 | 7.6 | .36 | — | — | — | — | — | — | — |
| 240 | Dimethylamine (.059) | 90 | 9.5 | .36 | — | — | — | — | — | — | — |
| 240 | Dimethylamine (.24) | 90 | 24.$^b$ | .36 | — | — | — | — | — | — | — |
| 240 | Dimethylamine (.12) | 100 | 15. | .18 | — | — | — | — | — | — | — |
| 240 | Dimethylamine (.12) | 90 | 6.0 | .087 | 100 | — | — | ≦.2 | 33 | — | 178 |
| 240 | Dimethylamine (.12) | 90 | 11.0 | .18 | — | — | — | — | — | — | — |
| 240 | Dimethylamine (.12) | 90 | 5.6 | .70 | — | — | — | — | — | — | — |
| 240 | Dimethylamine (.12) | 90 | 17.0 | 1.1 | — | — | — | — | — | — | — |
| 240 | Dimethylamine (.12) | 70 | 0.72 | 0.71 | — | — | — | — | .24 | no | 1250 |
| 240 | Aniline (.12) | 100 | 2.8$^c$ | .36 | — | — | — | — | 9.75 | no | 105 |
| 240 | Aniline (.12) | 100 | 3.3$^c$ | .36 | — | — | 81 | — | 37.7 | no | 320 |
| 240 | Aniline (.12) | 100 | 3.6$^c$ | .36 | — | — | — | — | 41.8 | no | 376 |

$^a$Mixture of 5d and 5d · HCl
$^b$Approx. 30 min induction period
$^c$Estimated from VCl conversion with stoichiometry, aniline/VCl consumption = 3.
$^d$R$^I$R$^{II}$NCH$_2$CH$_2$CONR$^I$R$^{II}$, R$^I$ = R$^{II}$ = CH$_3$
$^e$R$^I$R$^{II}$NCH$_2$CH$_2$CONR$^I$R$^{II}$, R$^I$ = H, R$^{II}$ = C$_6$H$_5$
$^f$Cl$^-$(PPh$_3$)$_3$$\overset{+}{P}$CH$_2$CH$_2$COR$^I$R$^{II}$
Ph = phenyl aniline (the 14th entry), 50 hr$^{-1}$ which is the slowest rate for reactions with one of the group ammonia, dimethylamine and aniline. The rates for dimethylamine may exceed about 1000 hr$^{-1}$ but will generally be in the range from about 100 hr$^{-1}$ to about 1000 hr$^{-1}$.

EXAMPLE 6

Example 2 was repeated employing alternate catalyst systems including platinum group metals and cobalt. The results are summarized in Table V.

TABLE V

Activity of Platinum Group and Related Metal Complexes in VCl Amidation$^a$

| Catalyst (mmol) | $P$(CO) (psi) | $NH_3$ (mol) | VCl Converted (mmol) | React. Time (HR) | Turnover$^b$ Rate (HR$^{-1}$) |
|---|---|---|---|---|---|
| Pd(PPh$_3$)$_4$ (.36) | 240 | .12 | 50.6$^c$ | 1.51 | 93. |

TABLE V-continued

Activity of Platinum Group and Related Metal Complexes in VCl Amidation[a]

| Catalyst (mmol) | $P$(CO) (psi) | $NH_3$ (mol) | VCl Converted (mmol) | React. Time (HR) | Turnover[b] Rate $(HR^{-1})$ |
|---|---|---|---|---|---|
| $Pt(PPh_3)_4$ (.36) | 240 | .12 | 1.4 | 3.25 | 1.2 |
| $Pt(PPh_3)_3$ (.36) | 240 | .12 | 1.7 | 1.67 | 2.8 |
| $Ir(PPh_3)_2(CO)Cl$ (.36) | 240 | .12 | 2.6 | 3.17 | 2.3 |
| $Rh(PPh_3)_3H(CO)$ (.36) | 240 | .12 | 1.8 | 2.5 | 2.0 |
| $Ru(PPh_3)_3Cl_2$ (.36) | 240 | .12 | 0.5 | 3.85 | 0.5 |
| $Co(PPh_3)_3Cl$ | 240 | .12 | 0.74 | 3.45 | 0.6 |

[a]At 100° C.
[b]mol VCl converted · mol cat$^{-1}$ · hr$^{-1}$.
[c]Calculated from rate of ammonia consumption. Ph = phenyl

EXAMPLE 7

Example 2 was repeated employing a catalyst of the form $PdCl_2(PPh_3)_2$; in each repetition 0.36 millimoles of catalyst and 0.12 moles of ammonia were introduced into the reactor and the reactor was pressurized to a carbon monoxide partial pressure of 240 pounds per square inch and the reaction was maintained at 100° C. for approximately 280 minutes. The results compared with results for $Pd(PPh_3)_4$ are as follows:

| Catalyst | Turnover Rate (mol · VCl · hr$^{-1}$ · mol · cat$^{-1}$) |
|---|---|
| $Pd(PPh_3*)_4$ | 93. |
| $PdCl_2(PPh_3)_2$ | ≦.80 |
| $PdCl_2(PPh_3)_2 + 2PPh_3$ | ≦.50 |

*Ph being phenyl

EXAMPLE 8

The effect of methyl substitution on vinyl chloride was determined by repeating Example 2 with the vinyl chloride being replaced in three separate examples by 48 grams of cis-, trans-, and 2-chlorpropene respectively, the quantities being selected to give approximately the same liquid volume in the reactor as obtained with the vinyl chloride monomer at 100° C. Reactions utilizing chloropropenes were conducted at 100° C. for approximately 280 minutes and the results are compared with those for vinyl chloride as follows:

| Reactant | Rate[a] (relative) | Products | Yield % (mol basis) |
|---|---|---|---|
| $H_2C=CHCl$ | 74 | $N(CH_2CH_2CONH_2)_3$ | 71 |
| | | + | 7 |
| | | $Cl^-HN(CH_2CH_2CONH_2)_3$ | |
| | | Acrylamide | 7 |
| | | + | 1 |
| | | $Cl^-Ph_3PCH_2CH_2CONH_2$* | |
| cis-$(CH_3)HC=CHCl$ | 2. | cis-$(CH_3)HC=CHCONH_2$ | 66 |
| trans-$(CH_3)HC=CHCl$ | 1. | trans-$(CH_3)HC=CHCONH_2$ | 51 |
| $H_2C=C(CH_3)Cl$ | 1. | $H_2C=C(CH_3)CONH_2$ | 90 |

[a]This is a rate calculated from chloroalkene conversion by chloride titration.
*Ph is phenyl

EXAMPLE 9

The effect of solvent upon the reaction of was investigated by repeating Example 2 employing 0.12 moles of ammonia, 0.36 moles of $Pd(PPh_3)_4$ catalyst where Ph is phenyl and charging the reactor employing a 1655 kPa partial pressure carbon monoxide. In one such run, the 19.1 grams of vinyl chloride charged to the reactor was augmented with 26.1 grams of acetonitrile and in another run the 19.1 grams vinyl chloride charged was augmented by 30.7 grams of toluene. The solvent quantities were selected to produce approximately the same volume within the reactor at 100° C. as is present when employing vinyl chloride. The reaction rates as measured by ammonia disappearance in mol.min$^{-1}$·10$^4$ were 13.0, 6.8 and 10.0 for vinyl chloride, acetonitrile/vinyl chloride, and toluene/vinyl chloride respectively. The product mix from the acetonitrile/vinyl chloride run yielded nitrilotripropanamide (57% on a mol basis), nitrilotripropanamide.HCl (18% on a mol basis), acrylamide (5.7% on a mol basis), and phosphonium salt (3.6 of on a mol basis).

EXAMPLE 10

Example 2 was repeated employing as the amine 0.12 moles of dimethylamine, and as catalyst 0.36 millimoles of $Pd(Ph_2PCH_2CH_2PPh_2)$ generated in situ from 0.184 grams of $Pd_3(TBAA)_3CHCl_3$ and 0.148 grams of 1,2-bis(diphenylphosphino)ethane. Conversion of the dimethylamine was 86% by weight in 21 hours after which an additional 0.10 mole of dimethylamine was charged to the reactor together with sufficient additional carbon monoxide so that the original total pressure was restored to the reactor at 90° C. The reaction was stopped after a total reaction time of 26 hours. The initial rate of dimethylamine consumption as measured by gas chromatography through a 26% conversion was $1.1 \times 10^{-4}$ mol·min$^{-1}$. This rate compares with $14 \times 10^{-4}$ mol·min$^{-1}$ obtained under the same conditions using $Pd(PPh_3)_4$. The reaction product was 3-dimethylamino-N,N-dimethylpropanamide at a 98% yield by weight.

EXAMPLE 11

Example 2 was repeated employing as the amine 21.9 grams (0.12 moles) of di-n-hexylamine the reaction being conducted for 20 hours. Following cooling and venting, the residue was stirred with 55 milliliters of ethanol and filtered. As measured by chloride titration, vinyl chloride conversion was 52 millimoles. Mass spectrometry showed the product to comprise di-n-hexylammonium chloride, N,N-di-n-hexylacrylamide, 3-(di-n-hexylamino)-N,N-di-n-hexylpropanamide and little or no unreacted di-n-hexylamine. A fraction of the ethanol extract was evaporated to dryness and dissolved in methanol-$d_4$. Toluene was added as an internal reference for quantitative $^1$H NMR analysis which revealed a product mix of N,N-di-n-hexylacrylamide (79% on a mol basis) and 3-(di-n-hexylamine)-N,N-di-n-hexylpropanamide (29% on a mol basis), the latter being estimated from overlapping peaks. Thus even extended chain primary and secondary amines can be employed in the practice of the instant invention.

From the foregoing examples it should be apparent that large and small alkylamines and weakly basic aromatic amines find utility in the practice of the instant invention. Further, particularly with palladium based catalyst, the reaction proceeds quite rapidly and can provide an extended catalyst life. Particularly, some dialkylamines possess the capability for rapidly removing acrylamide by Michael addition and rapidly reducing $Pd^{2+}$ complexes to $Pd(O)$ complexes under reaction conditions.

While a preferred embodiment of the invention has been shown and described in detail, it should be apparent that various modifications may be made thereto without departing from the scope of the claims that follow.

I claim:

1. In the amidation of vinyl chloride to acryl-amide or a N-substituted acrylamide, a two step process comprising, in a first step, reacting vinyl chloride with carbon monoxide and an amine represented by the structure $$HNR1_R{}^2$$

wherein $R^1$ and $R^2$ independently represent H, $C_1$-$C_4$ lower aklyl, phenyl, $C_1$-$C_4$ alkylphenyl, provided $R^1$ and $R^2$ are not both phenyl or $C_1$-$C_4$ alkylphenyl, in the presence of a catalytically effective amount of a palladium(O) triorganophosphine complex charged as such, or produced in situ, said complex having the stoichiometry:

$$Pd(PR_3)_n$$

wherein
R represents $C_1$-$C_4$ lower alkyl, phenyl, $C_1$-$C_4$ alkylphenyl, and cycloalkyl havign 4 to 6 ring carbon atoms; and,
n is an integer in the range from 2 to 6;
under elevated temperature and pressure reaction conditions, to form a major amount, on a molar basis, of the Michael adduct of said amine with said acrylamide, said conditions being a temperature in the range from above 80° C. to below a temperature at which said Michael adduct dissociates, and under a pressure in the range from about 200 psig but below 600 psig, in the absence of a tertiary amine;
whereby the rate of amidation with vinyl chloride is orders of magnitude faster than that of other monochloro-alkenes; and,
in a second step, converting said Michael adduct to said acrylamide.

2. The process of claim 1 wherein said amine is selected from the group consisting of ammonia, aniline and dimethylamine.

3. The process of claim 1 wherein said reaction proceeds at a turnover rate, measured as disappearance of said amine reactant, in excess of 50 hr$^{-1}$.

4. The process of claim 2 wherein said reaction proceeds at a turnover rate, measured as disappearance of said amine reactant, in the range from 50 hr$^{-1}$ to about 1000 hr$^{-1}$.

5. The process of claim 4 wherein said amine is dimethylamine and said reaction proceeds through more than 100 turnovers (moles of dimethylamine per mole of catalyst) without catalyst deactivation.

* * * * *